(12) United States Patent
Gore (10) Patent No.: US 10,279,172 B1
(45) Date of Patent: May 7, 2019

(54) MRI COMPATIBLE LEAD

(71) Applicant: Pinnacle Bionics, Inc., Commack, NY (US)

(72) Inventor: Dilys Gore, Monmouthshire (GB)

(*) Notice: Subject to any disclaimer, the term of this patent is extended or adjusted under 35 U.S.C. 154(b) by 0 days.

(21) Appl. No.: 15/096,089

(22) Filed: Apr. 11, 2016

Related U.S. Application Data

(63) Continuation of application No. 14/924,524, filed on Oct. 27, 2015, now abandoned, which is a continuation of application No. 14/660,764, filed on Mar. 17, 2015, now abandoned, which is a continuation of application No. 14/481,710, filed on Sep. 9, 2014, now abandoned.

(60) Provisional application No. 61/875,492, filed on Sep. 9, 2013.

(51) Int. Cl.
*A61N 1/00* (2006.01)
*A61N 1/08* (2006.01)
*A61N 1/05* (2006.01)

(52) U.S. Cl.
CPC .............. *A61N 1/08* (2013.01); *A61N 1/05* (2013.01); *A61N 2001/086* (2013.01)

(58) Field of Classification Search
CPC .................................. A61N 1/08; A61N 1/05
USPC ........................................................ 607/116
See application file for complete search history.

(56) References Cited

U.S. PATENT DOCUMENTS

| 8,380,277 B2 | 2/2013 | Atalar et al. | |
|---|---|---|---|
| 2010/0222857 A1 | 9/2010 | Halperin et al. | |
| 2011/0040343 A1 | 2/2011 | Johnson et al. | |
| 2011/0054582 A1* | 3/2011 | Dabney .................. | A61N 1/056 607/116 |
| 2011/0054584 A1* | 3/2011 | Alexander ........... | A61N 1/0551 607/116 |
| 2011/0066212 A1 | 3/2011 | Stevenson et al. | |

* cited by examiner

*Primary Examiner* — Nadia A Mahmood (57) ABSTRACT

A lead wire assembly apparatus for an implantable medical device (IMD), the apparatus including a lead having first and second ends and a plurality of separate conductive segments serially located therebetween; a cover defining at least one cavity situated about ends of adjacent conductive segments; and a fluid located in the at least one cavity and coupling the adjacent conductive segments to each other. The fluid electrically couples adjacent conductive segments to pass driving signals of the implantable medical device. The fluid may further attenuate induced signals generated by radiofrequency (RF) signals of a magnetic resonance (MR) system.

20 Claims, 9 Drawing Sheets

MRI COMPATIBLE LEAD

CROSS-REFERENCE TO RELATED APPLICATIONS

This application is a continuation of U.S. patent application Ser. No. 14/924,524 entitled, "MRI COMPATIBLE LEAD," filed on Oct. 27, 2015 which is a continuation of U.S. patent application Ser. No. 14/660,764 entitled, "MRI COMPATIBLE LEAD," filed on Mar. 17, 2015, which is a continuation of U.S. patent application Ser. No. 14/481,710 entitled, "MRI COMPATIBLE LEAD," filed on Sep. 9, 2014, which claims the benefit of U.S. Patent Application Ser. No. 61/875,492 entitled, "MRI COMPATIBLE LEAD," filed on Sep. 9, 2013. The contents of all of the above-noted applications are incorporated herein by reference as if set forth in full and priority to these applications is claimed to the full extent allowable under U.S. law and regulations.

FIELD OF THE PRESENT SYSTEM

The present system relates to an electrical lead which is compatible with use in magnetic resonance (MR) systems and, more particularly, to an electrical lead suitable for use in implanted devices which can be compatible for use within MR systems, and a method of operation thereof.

BACKGROUND OF THE PRESENT SYSTEM

Conventional implanted medical devices (IMDs) such as cardiac pacemakers, defibrillator or other neurostimulation devices (e.g., a phrenic nerve stimulators, deep brain stimulators, cochlear implants or vagal nerve stimulators) and the like are implanted within millions of patients. Unfortunately, these IMDs are incompatible for use with magnetic resonance (MR) imaging (MRI) methods for many reasons including that conventional IMDs may interact with fields (e.g., static and/or pulsed) of MR systems. For example, MR systems during imaging utilize radiofrequency (RF) emissions provided within a static magnetic field for eliciting emissions from a region of interest (ROI) such as a portion of a patient's anatomy. These elicited emissions are received by the MR system and are utilized for creating an image of the ROI by the MR system.

However, for a patient which has an IMD, the conductive portions such as lead wire of the IMD may act as an antenna to the RF emissions of the MR system which may result in RF heating of the lead wire due to induced standing waves within the lead wire. RF induced heating of the lead wire may cause heating of nearby tissue resulting in general patient discomfort and/or burning of the tissue. Accordingly, patients in which conventional IMDs are implanted cannot be safely scanned using MR methods and are typically scanned using less desirable imaging methods such as computed tomography (CT), X-ray methods, and the like, which emit ionizing radiation and may have inferior image resolution particularly of soft tissue present in the ROI.

Accordingly, embodiments of the present system may overcome these and/or other disadvantages of conventional systems and methods.

SUMMARY OF THE PRESENT SYSTEM

The system(s), device(s), method(s), arrangements(s), user interface(s), computer program(s), processes, etc. (hereinafter each of which will be referred to as system, unless the context indicates otherwise), described herein may address problems in prior art systems.

In accordance with embodiments of the present system, there is disclosed a lead wire assembly apparatus for an implantable medical device (IMD), the apparatus including a lead having first and second ends and a plurality of separate conductive segments serially located therebetween; a cover defining at least one cavity situated about ends of adjacent conductive segments; and a fluid located in the at least one cavity and coupling the adjacent conductive segments to each other. The fluid electrically couples adjacent conductive segments to pass driving signals of the implantable medical device. The fluid may further attenuate induced signals generated by radiofrequency (RF) signals of a magnetic resonance (MR) system. First and second ends of the lead may define a length of the lead wire which is greater than one-half wavelength length of radiofrequency (RF) signals generated by an MRI system. A length of at least one of the plurality of conductive segments may be less than one-half wavelength length of the radiofrequency (RF) signals generated by the MR system. The fluid may include a buffer, a conductive fluid or an ionic solution. In accordance with embodiments of the present system, the cavity is a first cavity and ends of adjacent conductive segments are located within the first cavity coupled to corresponding conductive cylinders with a first conductive cylinder of the corresponding conductive cylinders sized to fit within a second cavity formed by a second conductive cylinder of the corresponding conductive cylinders. The lead may be situated between and coupled to a signal generator and an interface probe.

In accordance with embodiments of the present system, an implantable medical device is provided including a signal generator configured to generate a driving signal; at least one controller configured to control the signal generator to generate the driving signal; a lead including first and second ends and a plurality of separate conductive segments serially located therebetween with the first end coupled to the signal generator, a cover defining at least one cavity, and a fluid located in the at least one cavity with the fluid electrically coupling adjacent conductive segments to each other; and an interface probe coupled to the second end of the lead. The fluid electrically couples adjacent conductive segments to pass the driving signal to the interface probe. The fluid may further attenuate induced signals generated by radiofrequency (RF) signals of a magnetic resonance (MR) system. The first and second ends of the lead may define a length of the lead which is greater than one-half wavelength length of radiofrequency (RF) signals generated by an MR system. A length of at least one of the plurality of conductive wire segments may be less than one-half wavelength length of the radiofrequency (RF) signals generated by the MR system. The fluid may include a buffer, a conductive fluid or an ionic solution. The cavity may be a first cavity and ends of adjacent conductive segments may be located within the first cavity coupled to corresponding conductive cylinders with a first conductive cylinder of the corresponding conductive cylinders sized to fit within a second cavity formed by a second conductive cylinder of the corresponding conductive cylinders.

In accordance with embodiments of the present system, a method of forming a lead for attenuating signals induced by radiofrequency (RF) signals of a magnetic resonance (MR) system, where the method includes acts of forming a lead having first and second ends and a plurality of separate conductive segments serially located therebetween; forming a cover defining at least one cavity in which adjacent ends of conductive segments are located; and electrically coupling adjacent conductive segments to each other within the at least one cavity using a fluid coupling.

BRIEF DESCRIPTION OF THE DRAWINGS

The present invention is explained in further detail in the following exemplary embodiments and with reference to the figures, where identical or similar elements are partly indicated by the same or similar reference numerals, and the features of various exemplary embodiments being combinable. In the drawings.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1A:
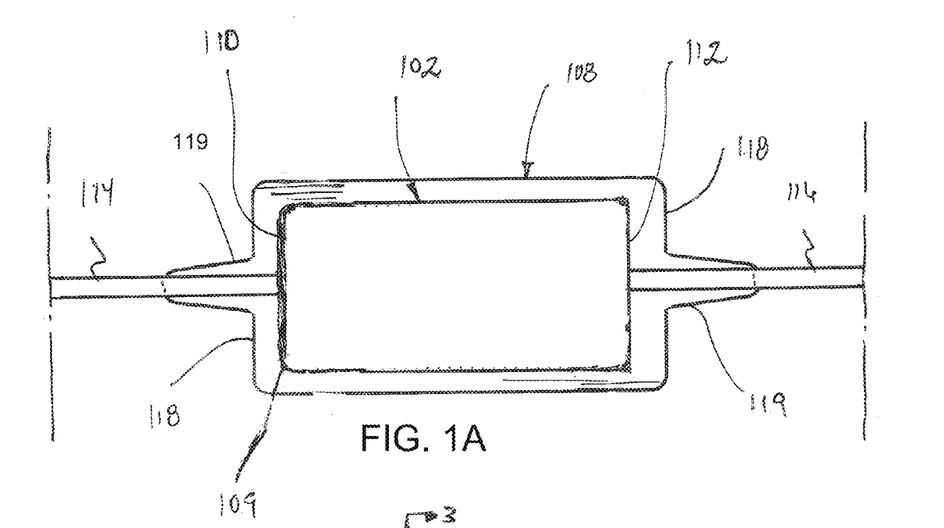
FIG. 1A shows a side view of a portion of a fluid-sealed connector (FSC) of an implantable medical device in accordance with embodiments of the present system.

FIG. 1A shows a side view of a portion of a fluid-sealed connector (FSC) 100 of an implantable medical device (IMD) such as an implantable cardiac probe, phrenic nerve lead, deep brain stimulator, cochlear implant, vagal nerve stimulator, etc., that may be utilized together with a magnetic resonance (MR) imaging system (MRI) in accordance with embodiments of the present system. The FSC 100 may include segment leads illustratively shown as first and second conductive segment lead wires (SLWs) 114 and 116, respectively and an outer cover 108 including an inner wall 102. The inner wall 102 may form a cavity 109 in which the SLWs 114, 116 are located at opposed end walls 118. The end walls 118 may operate to seal the cavity 109 with respect to the SLWs 114, 116 and/or to otherwise secure a position of the SLW 114 with respect to the SLW 116. The dimensions of the outer cover may be sized as desired though generally, the outer cover has a small length and width to facilitate implantation and/or to facilitate that a length of each of the SLWs satisfy other criteria as discussed further herein.

The term seal and formatives thereof as utilized herein is intended to indicate that a barrier is created (e.g., a fluidic barrier) by the outer cover (e.g., the outer cover 108) generally and between corresponding surfaces when present as discussed that resists escaping of for example a fluid through the barrier. In this way, in accordance with embodiments of the present system, a conductive material such as a liquid contained within the cavity, such as the cavity 109, cannot escape through the barrier or otherwise escape out of the cavity and matter such as fluids including liquid and gaseous fluids not contained therein cannot otherwise enter the cavity. In general it is significant in accordance with embodiments of the present system that what is contained within the cavity is significantly maintained in the cavity and material not contained in the cavity is substantially kept out. In accordance with embodiments of the present system, the outer cover, such as the outer cover 108 may be formed to provide a seal that may be impermeable, semi-permeable or permeable to given ions, given ionic solutions and/or given gases while being impermeable to the conductive material such as the given ionic solution contained therein.

In accordance with further embodiments of the present system, the outer cover described herein and corresponding FSC may be formed to not provide a seal (i.e., in these embodiments, the FSC is not "sealed") and thereby may be semi-permeable or permeable to given ions, given ionic solutions and/or given gases including to the conductive material such as the given ionic solution contained therein. For example, the outer cover may be purposefully formed with a "leaky seal" thereby enabling ions, ionic solutions and/or gases including the conductive material initially placed within the cavity, to pass in and out of the outer cover through the leaky seal. In other embodiments, the outer cover may be formed having pores and/or may be provided with holes after formation that renders the outer cover semi-permeable or permeable to ions, ionic solutions and/or gases including the conductive material initially placed within the cavity. In an IMD wherein the environment of the implant and an FSC that is not sealed typically includes electrically conductive biological gases and/or biological liquids, conductivity between conductors within the cavity as described herein is maintained in these embodiments even though the outer cover is not sealed. For example, in an embodiment wherein the outer cover is not sealed, conductivity between conductors within the cavity as described herein is maintained by one or more of the conductive material initially placed within the cavity, the biological gas(es) and/or the biological liquid(s) being within the cavity in contact with the conductors.

In accordance with embodiments of the present system, a first end 110 of the outer cover 108 may be sealed (e.g., glued, formed, ultrasound welding, laser welding, RF welding, glass seal, metal forming, elastomer layer bonding, UV-cured adhesive seal, any combinations thereof, and/or other suitable technology on consideration of the materials utilized that provides a seal such as a hermetic seam, etc.) to the SLW 114 to seal the cavity 109 with regard to the first end 110 and the SLW 114. In addition to the seal, the first end 110 of the outer cover 108 may be further structurally connected to the SLW 114 to secure a position of the SLW 114 in relation to the SLW 116. For example, one or more methods such as described above may be utilized to provide a seal while one or more of the methods is utilized to provide a further structural connection with or without providing an additional seal. Similarly, a second end 112 of the outer cover 108 may be sealed to the SLW 116 to provide a barrier between the cavity 109 and the SLW 116. Further, the second end 112 of the outer cover 108 may provide a seal and may be additionally structurally connected to the SLW 116 to secure the position of the SLW 116 in relation to the SLW 114. Details within the cavity 109 are excluded from this view for the sake of clarity.

Figure 1B:
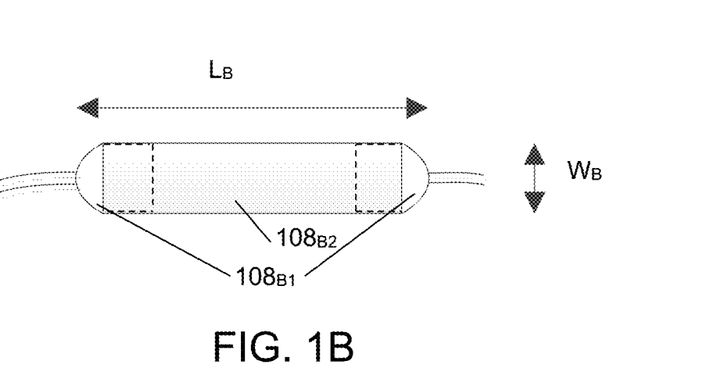
FIG. 1B shows a side view of a portion of an FSC of an implantable medical device in accordance with embodiments of the present system.
Figure 1C:
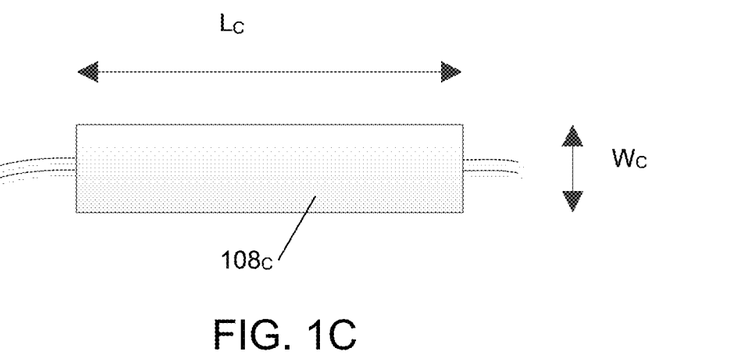
FIG. 1C shows a side view of a portion of an FSC of an implantable medical device in accordance with embodiments of the present system.

In accordance with embodiments of the present system, the opposed end walls 118 may be sealed about the first and second SLWs 114 and 116, respectively, at seals 119 which may be drawn away from the cavity 109 of the outer cover 108. However, it is also envisioned that the seals 119 may fit flush with exterior portions of the opposed end walls 118 in accordance with further embodiments of the present system such as shown in FIG. 1C. FIG. 1C shows a side view of a portion of an FSC of an implantable medical device in accordance with embodiments of the present system wherein seals of an outer cover 108C fit flush with the opposed end walls. The outer cover 108$_C$ has a length $L_C$ and a width $W_C$ that may vary in scale. In accordance with embodiments of the present system, the length $L_C$ and the width $W_C$ for example may each be within a range of 1 to 0.1 inches (e.g., 0.113 inches), within a range of 0.5 to 0.1 inches, within a range of 0.3 to 0.1 inches as desired. The length $L_C$ may have different dimensions from the width $W_C$ and may vary within a different range and larger and smaller dimensions are conceived suitable for an implantable device. It should be appreciated that the dimensions for all of the embodiments described herein may also vary as in the embodiment shown in FIG. 1C.

The first and second SLWs 114 and 116, respectively, may be coated to enhance sealing of the cavity. In accordance with embodiments of the present system, the cavity 109 may be hermetically sealed to contain fluid within the cavity as discussed further herein. The outer cover 108 may be formed from any suitable material or combination of materials (e.g., a non-conductive material) such as a ceramic, a polymer, etc., to seal the cavity and may further act to hold the first and second SLWs 114, and 116, respectively, in place relative to each other. The material of the outer cover should be selected with consideration to the environment in which the outer cover is placed during use. For example, in an embodiment wherein the outer cover is intended for implantation, the outer cover material should be selected to be suitable for implantation as appreciated such as a biocompatible material. While the outer cover is illustratively shown having differing forms in the various views provided in the figures, other shapes and forms may be suitably applied as long as the provided outer cover seals an inside of the cavity from an outside of the cavity. For example, FIG. 1B shows a side view of a portion of an FSC of an implantable medical device in accordance with embodiments of the present system wherein an outer cover is formed by two end caps 108$_{B1}$ and an outer sleeve 108B$_2$. As shown by dashed lines, the two end caps 108$_{B1}$ extend into the outer sleeve 108B$_2$ for a distance as desired to enable the outer cover to provide a seal as previously discussed. The two end caps 108$_{B1}$ and/or corresponding extensions may be sealed to the outer sleeve 108B$_2$ using any suitable sealing technology such as described herein. Further, each end of the outer sleeve 108$_{B2}$ may be crimped, tied (e.g., utilizing a tie-wrap), etc., to a corresponding end cap 108$_{B1}$ to facilitate sealing. As readily appreciated, the outer cover and corresponding SLWs may be sized (e.g., the length $L_B$ and the width $W_B$) and for example sealed as previously discussed.

Figure 1D:
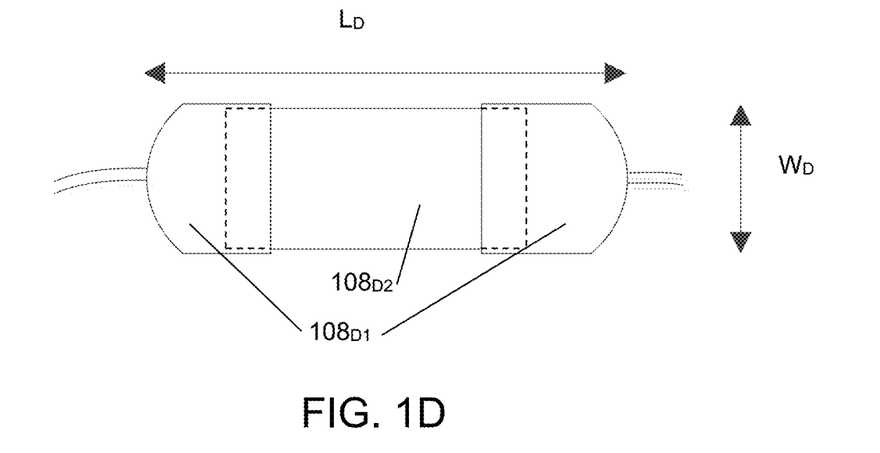
FIG. 1D shows a side view of a portion of an FSC of an implantable medical device in accordance with embodiments of the present system.
Figure 2:
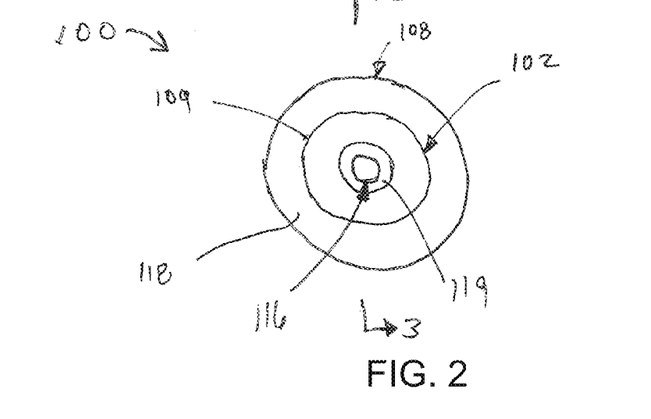
FIG. 2 shows an end view of a portion of the FSC of FIG. 1A in accordance with embodiments of the present system.

FIG. 1D shows a side view of a portion of an FSC of an implantable medical device in accordance with embodiments of the present system wherein an outer cover is formed by two end caps 108$_{D1}$ and an inner sleeve 108$_{D2}$. As shown by dashed lines, the inner sleeve 108$_{D2}$ extends into the two end caps 108$_{D1}$ for a distance as desired to enable the outer cover to provide a seal as previously discussed. The inner sleeve 108$_{D2}$ and/or corresponding extensions may be sealed to the two end caps 108$_{D1}$ using any suitable sealing technology such as described herein. Further, each of the two end caps 108$_{D1}$ may be crimped, tied (e.g., utilizing a tie-wrap), etc., to a corresponding end of the inner sleeve 108$_{D2}$ to facilitate sealing. As readily appreciated, the outer cover and corresponding SLWs may be sized (e.g., the length $L_D$ and the width $W_D$) and for example sealed as previously discussed. FIG. 2 shows an end view of a portion of the FSC 100 of FIG. 1A in accordance with embodiments of the present system. The inner wall 102 may be situated about the cavity 109 formed by the outer cover 108 and may be coupled to an SLW such as the SLW 116. The outer cover 108 including the opposed end wall 118 and the seal 119 may seal the cavity 109 as discussed herein. The outer cover 108 may further provide electrical isolation and may be formed having a given thickness for example suitable for a desired electrical isolation. An end view of the other end may be similar and is not shown for the sake of brevity.

Figure 3:
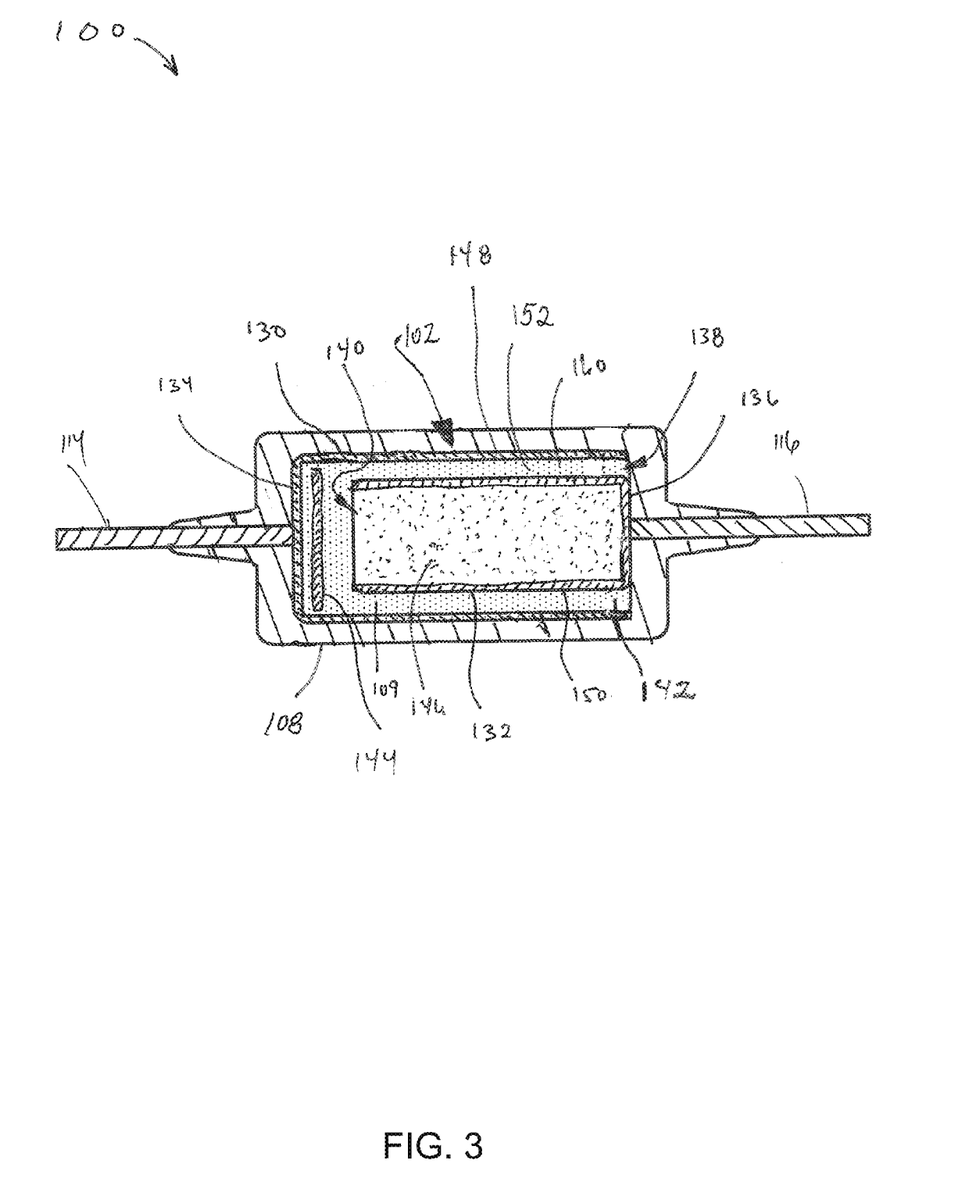
FIG. 3 shows a cutaway view of a portion of the FSC taken along lines 3-3 of FIG. 3 in accordance with embodiments of the present system.

FIG. 3 shows a cutaway view of a portion of the FSC 100 taken along lines 3-3 of FIG. 2 in accordance with embodiments of the present system. The SLW 114 is shown electrically coupled to a conductor illustratively shown as a first 130 cylinder which is conductive. The first cylinder 130 may include a cylindrical wall portion 148 defining a cavity 152 having an open end 138. The cylindrical wall portion 148 is electrically coupled to an adjacent SLW such as the SLW 114 using any suitable method via an end wall 134. A second conductor illustratively shown as a second cylinder 132 may be shaped similarly to the first cylinder 130 but may be sized such that at least a portion of the second cylinder 132 may fit within the cavity 152 of the first cylinder 130 with a desired spacing between portions of the first and second cylinders 130, 132, respectively. In accordance with embodiments of the present system, the first and second conductors (e.g., the cylinders 130, 132) do not physically contact each other. Accordingly, the second cylinder 132 may include a cylindrical wall portion 150 spaced apart from the cylindrical wall portion 148 of the first cylinder 130. In accordance with embodiments of the present system, the second cylinder 132 may be hollow defining a cavity 146 having an open end 140. In accordance with further embodiments of the present system, the second cylinder 132 may be a solid cylinder such that there is no cavity within the second cylinder 132. The cylindrical wall portion 150 is electrically coupled to an adjacent SLW such as the SLW 116 using any suitable method via an end wall 136. In accordance with embodiments of the present system that may be suitably employed, the SLW and conductor may be formed together with the corresponding conductor as a single continuous conductor such that no separate coupling therebetween is required.

A disc 144 may optionally be situated within the cavity 152 of the first cylinder 130 and may isolate the first and second cylinders 130 and 132, respectively, from each other as may be desired. Accordingly, the disc 144 may have a similar cross section as a cross section defined by the cylindrical wall 148 of the first cylinder 130. The disc 144 may be formed from any suitable material such as a ceramic, a polymer, etc., which may act as a dielectric isolator. Although the second cylinder 132 is illustratively shown spaced apart from the disc 144, in accordance with further embodiments of the present system, the second cylinder 132 may rest against the disc 144. In these embodiments, the disc 144 may provide positional stability to the second cylinder 132 with respect to the spacing from the first cylinder 130.

In accordance with embodiments of the present system, a conductive material such as a gel, a fluid, etc., illustratively discussed as a fluid 160 which may be formed as a buffer, an ionic solution, a conductive fluid, etc., may be situated within the cavity 109 and the cavity 146 when present (i.e., in an embodiment wherein the second cylinder 132 is hollow). Thus, the first and second cylinders 130, 132, respectively, electrically insulated from each other due to the two physically separated metallic conductors (e.g., the first and second cylinders 130 and 132) are electrically coupled via the fluid 160. In accordance with embodiments of the present system, the fluid 160 may further attenuate undesirable signals such as signals that otherwise may be induced by radiofrequency (RF) signals into the SLWs 114, 116 from external sources such as from an RF signal emitted from an MR system.

In the embodiment shown in FIG. 3, the cylinder 130 is illustratively shown directly adjacent to the inner wall 102 of the outer cover 108 which in the embodiment shown, may provide positional stability to the first cylinder 130. In accordance with further embodiments of the present system, one or more portions of the first cylinder 130 (e.g., one or more of the cylindrical wall portion 148 and the end wall 134) may be spaced apart from the outer cover 108 with the spacing filled by the conductive material (e.g., the fluid 160). Further, in the embodiment shown in FIG. 3, the cylinder 132 is illustratively shown directly adjacent to the inner wall 102 of the outer cover 108 which in the embodiment shown, may provide positional stability to the second cylinder 132. In accordance with further embodiments of the present system, one or more portions of the second cylinder 132 (e.g., the end wall 134) may be spaced apart from the outer cover 108 with the spacing filled by the conductive material (e.g., the fluid 160).

It is envisioned that embodiments of the present system may provide a connector which may include metallic conductors (e.g., first and second cylinders) which may each be individually attached to an adjacent SLW (e.g., metallic wire) external to the corresponding metallic conductor. The metallic conductors may be coupled to each other such as via a fluid such as an ionic fluid that may be situated between the metallic conductors. Accordingly, an electrical coupling between the metallic conductors inside the connector (e.g., the FSC 100) may be obtained via the fluid. A shape and dimension of the metallic conductors and a strength (e.g., conductivity) and chemical composition of the fluid (e.g., the ionic solution) may be adjusted as required.

For example in a case wherein the conductive material is a conductive liquid, a saline solution with 0.9% (or 9 gram/1 liter) of sodium chloride (NaCl electrolyte) dissolved in water may be utilized within the cavity in accordance with embodiments of the present system. The conductivity of this saline fluid is approximately 17.0 mS/cm (milli siemens per cm). Other appropriate concentrations and/or solutions that conduct ionically may also be used. In accordance with embodiments of the present system, the conductivity of a conductive solution may be increased which may enable smaller conductors and outside cover or decreased as desired and still operate in accordance with embodiments of the present system. Further, a 3.0% NaCl solution (or 30 gram/1 liter water) having a conductivity of approximately 48.6 mS/cm, a 5.0% NaCl solution having a conductivity of approximately 81.0 mS/cm or a 0.5% NaCl solution having a conductivity of approximately 9.48 mS/cm may be utilized in accordance with embodiments of the present system though other concentrations and/or ionic solutions (e.g., potassium chloride solution, KCl) may be suitably applied.

For example, organic acids or other fluids with a conductivity lower than metals may be suitably utilized in accordance with embodiments of the present system. As readily appreciated, the impedance of the FSC will depend on the conductivity of the conductive material (e.g., the concentration of an ionic solution), the surface area of the conductors within the cavity and the separation between the conductors. The impedance of the FSC may be adjusted as desired by changing any one or more of these variables. As desired, a different ionic solution for example such as an acid may be used as these have much higher conductivity than the saline solution. However, for an implantable device, the biocompatibility of the conductive material such as saline may be a consideration for selection of the conductive material as well as the suitability of the conductive material to the conductors and the outer cover.

In accordance with embodiments of the present system, the conductors within the cavity may be formed from a metal such as stainless steel, platinum, titanium, gold, silver, or other conductive materials such as graphite or graphene carbon nanotubes. In any event, the material of the conductors is selected to have a greater conductivity than the conductive fluid. In addition, in accordance with embodiments of the present system, the conductors may have a porous surface, may have increased surface roughness and/or may have a corrugated shape to improve conductivity between the conductors resultant with the fluid. In accordance with embodiments of the present system, in place of the first and second cylinders, the contacts may have other configurations such as dual wire electrodes in parallel (i.e. radially) or axially (i.e., butt-to-butt) comprised of two conductors in the same axis though not making physical contact, dual helical (coil shape) conductors, dual spiral conductors, dual disk conductors, dual plate conductors, etc.

Figure 12A:
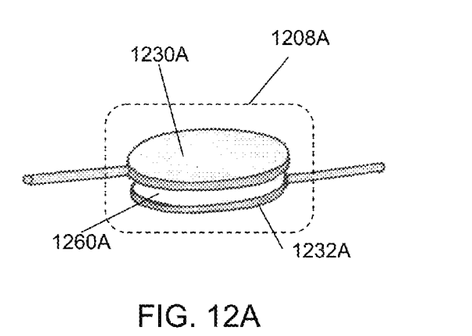
FIG. 12A shows a cutaway side view of a portion of an FSC in accordance with embodiments of the present system.
Figure 12B:
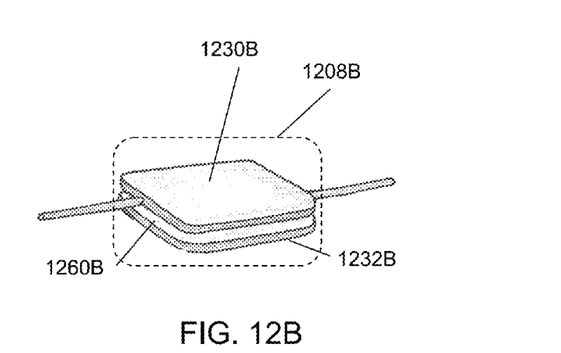
FIG. 12B shows a cutaway side view of a portion of an FSC in accordance with embodiments of the present system.
Figure 12C:
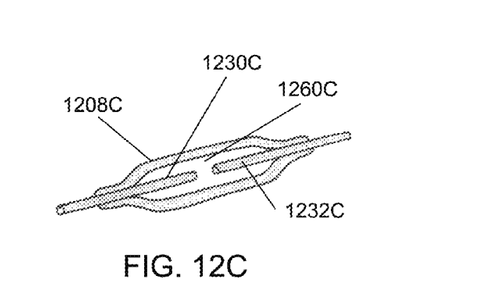
FIG. 12C shows a cutaway side view of a portion of an FSC in accordance with embodiments of the present system.
Figure 12D:
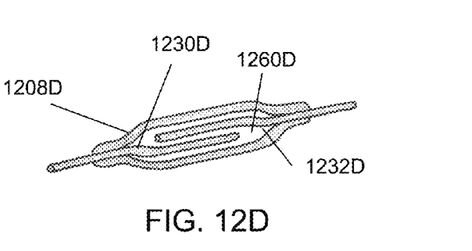
FIG. 12D shows a cutaway side view of a portion of an FSC in accordance with embodiments of the present system.
Figure 12E:
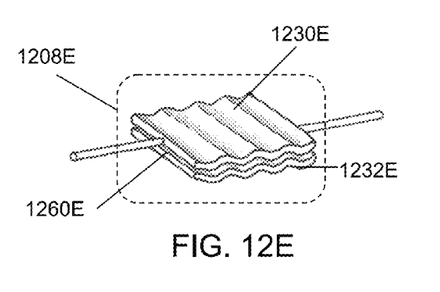
FIG. 12E shows a cutaway side view of a portion of an FSC in accordance with embodiments of the present system.
Figure 12F:
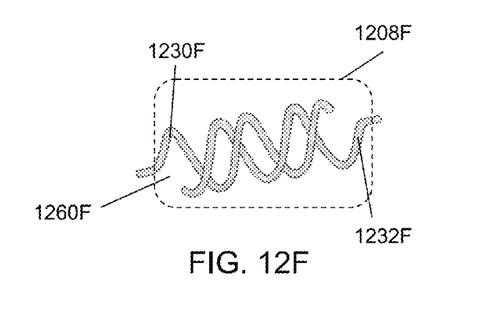
FIG. 12F shows a cutaway side view of a portion of an FSC in accordance with embodiments of the present system.

For example, FIG. 12A shows a cutaway side view of a portion of an FSC in accordance with embodiments of the present system where contacts 1230A, 1232A are similarly cylindrically shaped (e.g., dual disk conductors) and include an outer cover 1208A containing a conductive fluid 1260A. FIG. 12B shows a cutaway side view of a portion of an FSC in accordance with embodiments of the present system where contacts 1230B, 1232B are similarly rectangular (e.g., square dual plate conductors) shaped with rounded corners though other similar embodiments may have right angles or substantially right angled corners and include an outer cover 1208B containing a conductive fluid 1260B. FIG. 12C shows a cutaway side view of a portion of an FSC in accordance with embodiments of the present system where contacts 1230C, 1232C are similarly elongated conductors (e.g., wire conductors) extending towards each other (e.g., dual wire electrodes in parallel axially, butt-to-butt) and include an outer cover 1208C similar to the outer cover 108 shown in FIGS. 1A, 3 containing a conductive fluid 1260C. One or more of the contacts 1230C, 1232C may be provided as continuous extensions of corresponding SLWs or may be separately coupled thereto. FIG. 12D shows a cutaway side view of a portion of an FSC in accordance with embodiments of the present system where contacts 1230D, 1232D are similarly elongated conductors (e.g., dual wire conductors in parallel arranged radially) extending towards and past each other without touching and include an outer cover 1208D similar to the outer cover 108 shown in FIGS. 1A, 3 containing a conductive fluid 1260D. One or more of the contacts 1230D, 1232D may be provided as continuous extensions of corresponding SLWs or may be separately coupled thereto. FIG. 12E shows a cutaway side view of a portion of an FSC in accordance with embodiments of the present system wherein contacts are similarly complementary shaped ridged contacts 1230E, 1232E and include an outer cover 1208E containing a conductive fluid 1260E. FIG. 12F shows a cutaway side view of a portion of an FSC in accordance with embodiments of the present system where contacts 1230F, 1232F are similarly elongated conductors (e.g., wire conductors) extending towards and past each other intertwined (e.g., dual helical coil shape, conductors, dual spiral conductors, etc.) without touching and include an outer cover 1208F containing a conductive fluid 1260F. One or more of the contacts 1230F, 1232F may be provided as continuous extensions of corresponding SLWs or may be separately coupled thereto.

In accordance with embodiments of the present system, the surface of one or more of the conductors of these and/or other embodiments may be porous, may have holes (e.g., arranged randomly along one or more of the conductors or arranged in a pattern), may have ridges, or may have a corrugated surface shape (alternate ridges and grooves) to increase surface contact with the fluid and thereby improve the conductivity between the conductors. As appreciated, better conductivity enables reducing a size of the FSC while still operating (e.g., conducting physiological pulses while reducing incidence of induced standing waves) in accordance with embodiments of the present system. In accordance with embodiments of the present system, the conductors may be of the same material, dissimilar materials, and/or may be coated with different materials from the underlying portion to provide desired characteristics (e.g., to increase conductivity of the conductors and/or to provide suitability to the conductive material contained within the cavity of the outer cover).

Accordingly, embodiments of the present system may provide a lead wire (e.g., the FSC 100) suitable for an IMD which may be used in or in the vicinity of radiofrequency (RF) emitters such as an MR system including a magnetic resonance imaging (MRI) system. Embodiments of the present system may reduce or otherwise entirely prevent undesirable interaction with RF emitters which may, for example, contribute to radiofrequency (RF) induced heating of metallic lead wires which may cause thermal injury to tissue near to the lead such as at an end of the lead (e.g. a lead tip) and/or an implanted probe.

For example, RF induced heating of a conventional lead (CL) may occur when the CL acts as an antenna capable of receiving and supporting the frequency of an MR system's RF field. RF induced heating of the lead wire is most pronounced when a length of the lead wire (e.g., CL) in implanted tissue (i.e., dielectric medium) is close to a resonance length (e.g., one-half wavelength) of the RF emissions of the MR system. For example, an MR system that provides an RF field of 1.5 Tesla operates at approximately 64 MHz and thereby provides an in air equivalent one-half wavelength of approximately 2.3 m. An MR system that provides an RF field of 3.0 Tesla operates at approximately 128 MHz and thereby provides an in air equivalent one-half wavelength of approximately 1.2 m. An MR system that provides an RF field of 7.0 Tesla operates at approximately 300 MHz and thereby provides an in-air equivalent one-half wavelength of approximately 0.5 m.

However, in accordance with embodiments of the present system, it is found that within the body, due to the relative dielectric constant, the one-half wavelength may be reduced by approximately a factor of 90 i.e., to 26 cm for a 1.5 Tesla system, 14 cm for a 3.0 Tesla system and 6 cm for a 7.0 Tesla system.

In accordance with embodiments of the present system, lead segments (e.g., SLW such as each of SLW 114, 116) including a length of the corresponding conductor within the cavity (e.g., cylinders 130, 132) shorter than the one-half wavelength length of the RF signal of an MRI system may be employed (e.g., less than half of the wavelength length or less than 6 cm for a 7T MR system) and may reduce or entirely prevent the formation of standing waves induced by the RF emissions of the MR system.

Embodiments of the present system may provide a lead suitable (e.g., FSC 100) for use in an MR environment in which a lead having a plurality of segments (e.g., lead segments such as SLWs 114 and 116) each of which may be formed from a metallic material as described and which may have a length of less than one-half wavelength of an emitted signal from an RF coil of an MR system employed (e.g., intended to be used for the clinical investigation). The plurality of lead segments are serially coupled together in such a way that the subsequent full length lead wire (e.g., from an outside end of SLW 114 to an outside end of SLW 116) is able to conduct physiological stimulating or recording signals so as to reduce or entirely prevent (e.g., by fully or partially attenuating) the transmission of the RF signals thus greatly reducing (e.g., reducing by more than 90%) or totally eliminating the formation of standing waves generated as a result of the RF emissions and minimizing an RF heating effect upon an object in close proximity to the lead.

Accordingly, embodiments of the present system may provide an implanted device compatible for use in conjunction with MR systems as well as components for the implanted device (such as a lead wire or lead wire segment connector) and associated methods of construction and use. Embodiments of the present system may overcome potential issues associated with transmission by lead wires of the implanted device such as induced signal components associated with the radio frequency (RF) signal of the MR system which may cause heating of metallic lead wires and may cause thermal injury to adjacent tissue.

In accordance with embodiments of the present invention, a method is provided for constructing an implanted medical device that may be used in conjunction with a MR system. For example, the implanted medical device may be a cardiac pacemaker, defibrillator, nerve stimulator, brain stimulator, or cochlear implant. The implanted medical device may include at least one component that may be implanted in a patient and may include external components. The method may include acts of providing a lead wire for the implanted medical device having a total lead wire length greater than one-half of the MRI system's RF signal wavelength length and/or adapting the lead wire to inhibit transmission of the MR system's RF signal as described. In this regard, the one-half wavelength length dimension may be approximately six centimeters for a 7.0 Tesla MR system, but may be longer or shorter for other MR systems.

Any adaptation to the lead wire that inhibits transmission therein of the MR system's RF signal may be utilized in accordance with present invention. In accordance with embodiments of the present system the lead wire may be a metallic lead wire and the act of adapting may include 1) segmenting the lead wire into segments (e.g., each of SLW 114, 116) each having segment lengths less than one-half wavelength length of MR system's RF signal, and 2) connecting the segments in a manner that inhibits transmission of the RF signal between the connected segments such as described herein. For example, the coupling between the first 130 cylinder and the second cylinder 132 via the conductive material such as the fluid 160 may operate interposed between the segments to selectively transmit a signal of the implanted medical device and inhibit an induced transmission of the MR system's RF signal. Where the signal of the implanted medical device has a frequency different than the RF signal, the lead wire including the conductors (e.g., the FSC 100, 400, 800, etc.) may thus function to pass the medical device signal and inhibit transmission of the RF signal on a frequency dependent basis. In this way in accordance with embodiments of the present system, the induced RF component may be selectively removed.

It will be appreciated that, in the context of an implantable device, it is desirable to achieve this RF inhibiting function in a compact design. Accordingly, RF filters deployed in other contexts may not be suitable for use in this context. In the embodiments of the present system described herein, a conductive material such as a buffer material (e.g., the solution 160) is provided at least between the first and second conductors (e.g., the first and second cylinders) of the first and second segments (e.g., each of the SLWs 114, 116) of the lead wire. The buffer material may be a conductive fluid having appropriate signal properties with respect to the configuration of the connector (e.g., the spacing between the leads). For example, the buffer material may be an ionic solution.

In accordance with another aspect of the present system, an implanted medical device may be provided for use in conjunction with an MR system. The implanted medical device may include a signal generator providing a stimulus signal for use by the implanted medical device, a stimulus unit (e.g., an interface probe) for receiving the stimulus signal and applying a stimulus to a patient, and one or more lead wires (e.g., the FSC 100, 400, 800, etc.) for use in transmitting the stimulus signal between the signal generator and the stimulus unit. Depending on the nature of the implanted medical device, the signal generator may be part of the implanted unit or may be part of an external unit. The lead wire may have a total lead wire length greater than one-half wavelength length of an MR system's radio frequency signal and may be adapted to inhibit transmission therein of the MR system's RF signal. The lead wire may be constructed in accordance with embodiments of the present system.

In accordance with a still further aspect of the present system, an accessory component of an implanted medical device for use in connection with a MR system may be provided. The accessory component may include a lead wire for the implanted medical device having a total lead wire length greater than one-half wavelength length of the MR system's RF signal as described herein which may inhibit an induced transmission therein of the MR system's RF signal. The lead wire may be constructed in segments (e.g., each of the FSWs 114, 116) each having a length less than one-half wavelength length of the MR system's RF signal with the cavity and conductive material interposed between segments as described herein.

In accordance with a still further aspect of the present system, a lead line (e.g., FSC) of an implanted medical device is provided for use in conjunction with a MR system. The lead wire may have a total lead wire length greater than one-half wavelength length of the MRI system's RF signal and may be composed of segments having segment lengths less than one-half of the noted wavelength length. The connector may include a first conductor associated with a first connected segment of the lead wire (e.g., a conductor associated with the SLW 114), a second conductor associated with a second connected segment of the lead wire (e.g., a conductor associated with the SLW 116), and a gap situated between the first and second conductors with an appropriate buffering material, such as an ionic fluid, disposed in the gap that may selectively transmit a signal of the implanted medical device and may inhibit an induced transmission of the MR system's RF signal.

Figures 4, 5, 6, 7:
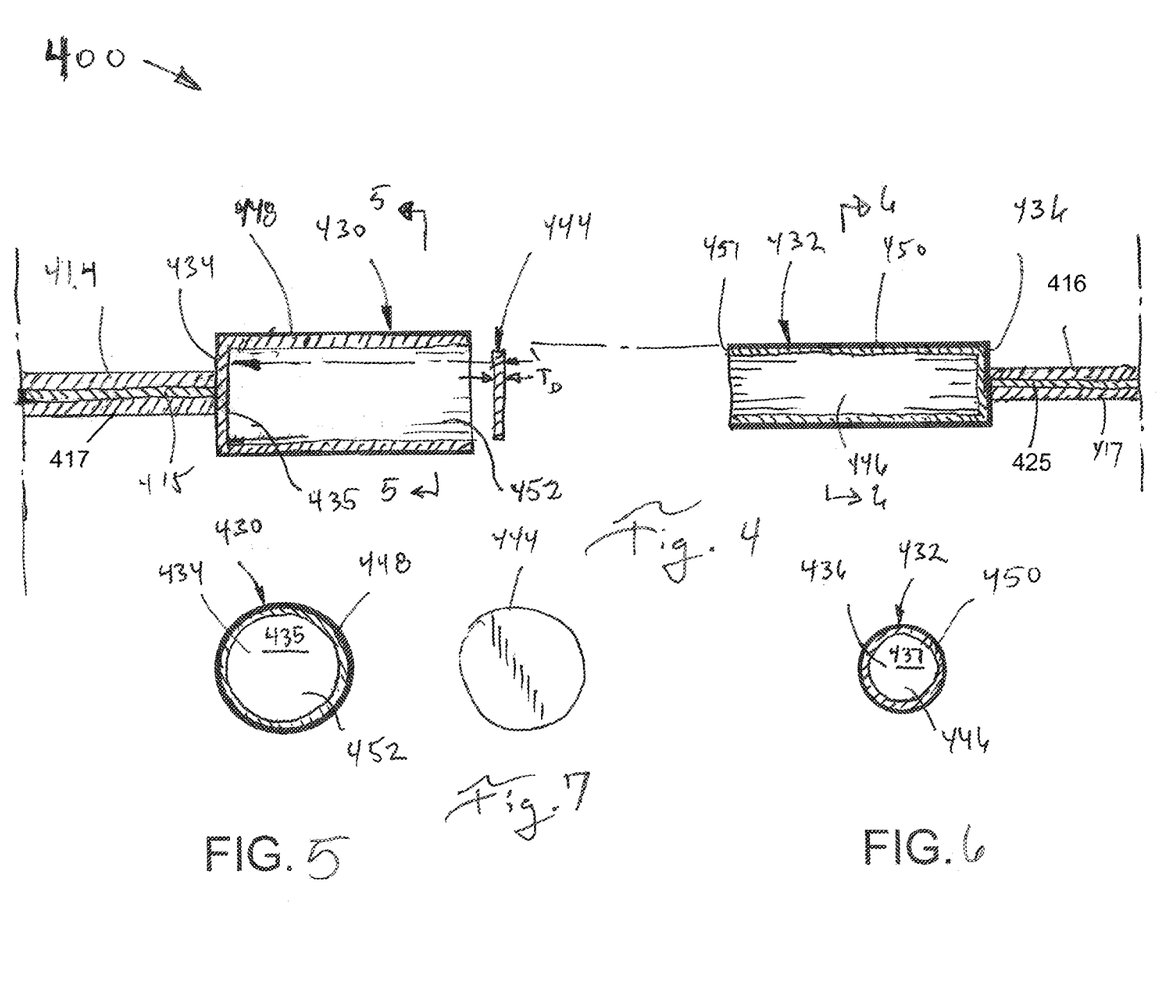
FIG. 4 shows a cutaway exploded side view of a portion of an FSC in accordance with embodiments of the present system.
FIG. 5 shows a cutaway view of a portion of the first cylinder of an FSC taken along lines 5-5 of FIG. 4 in accordance with embodiments of the present system.
FIG. 6 shows a cutaway view of a portion of the second cylinder of the FSC taken along lines 6-6 of FIG. 4 in accordance with embodiments of the present system.
FIG. 7 shows an end view of a portion of the disc of FIG. 4 in accordance with embodiments of the present system.

FIG. 4 shows a cutaway exploded side view of a portion of an FSC 400 in accordance with embodiments of the present system. The FSC 400 may be similar to the FSC 100 and may include first and second conductors illustratively shown as first and second cylinders 430, 432, respectively, a disc 444, and first and second SLWs 414, 416, respectively. The first cylinder 430 may include a cylindrical wall 448 defining a cavity 452 and having an end wall 434. Similarly, in accordance with embodiments of the present system, the second cylinder 432 may include a cylindrical wall 450 defining a cavity 446 and having an end wall 436 or the second cylinder may be solid as described herein.

The first SLW 414 may be coupled to (electrically and physically) an end wall 434 of the first cylinder 430 via a conductive layer 415 and the second SLW 416 may be coupled to (electrically and physically) the end wall 436 of the second cylinder 432 via a conductive layer 425. The first and second cylinders 430, 432, respectively, may be at least partially formed from a conductive material so as to be electrically coupled to the respectively attached SLWs 414, 416. The first and second SLWs 414, 416 may include an insulating layer 417 which may provide physical and/or electrical isolation to the respective conductive layer 415, 425 (i.e., by surrounding the respective conductive layer as shown) of the respective first and second SLW 414, 416.

The disc 444 may be situated between an end wall 451 of the cylindrical wall 450 of the second cylinder 432 and an interior portion 435 of the end wall 434 of the first cylinder 430 and may be formed from one or more insulating materials so as to insulate adjacent portions of the first and second cylinders 430, 432, respectively, from each other. A thickness $T_D$ of the disc 444 may be varied to provide a desired level of isolation and/or attenuation of desired signals. At least a portion of the cavity 452 of the first cylinder 430 and a portion of the cavity 446 of the second cylinder 432, when present, may be filled with a conductive material, (e.g., a fluid) such as an ionic fluid formed in accordance with embodiments of the present system.

FIG. 5 shows a cutaway view of a portion of the first cylinder 430 of the FSC 400 taken along lines 5-5 of FIG. 4 in accordance with embodiments of the present system. The end wall 434 is coupled to the cylindrical wall 448 and includes the interior portion 435 which may at least partially seal an end of the cavity 452.

FIG. 6 shows a cutaway view of a portion of the second cylinder 432 of the FSC 400 taken along lines 6-6 of FIG. 4 in accordance with embodiments of the present system. The end wall 436 is coupled to the cylindrical wall 450 and includes the interior portion 437 (e.g., in embodiments wherein the second cylinder is hollow) which may at least partially seal an end of the cavity 446.

The first and second cylinders 430, 432, respectively, may have similar cross-sectional shapes (e.g., round in the present embodiments) but may be sized differently such that the second cylinder 432 may fit within at least a portion of the cavity 452 of the first cylinder 430. Without limitation, although a round cross-sectional shape is shown for the first and second cylinders 430, 432, other shapes including cross sectional shapes such as ellipsoid, polygonal, etc., are also envisioned as may be desired.

FIG. 7 shows an end view of a portion of the disc 444 of FIG. 4 in accordance with embodiments of the present system. The disc 444 may have a cross section which may be similar to the cross sectional shape of the first cylinder 430. However, the disc 444 may be sized (e.g., in diameter) such that it is smaller than a diameter of an interior surface of the cylindrical wall 448 so as to fit within the cavity 452 of the first cylinder 430.

Figure 8:
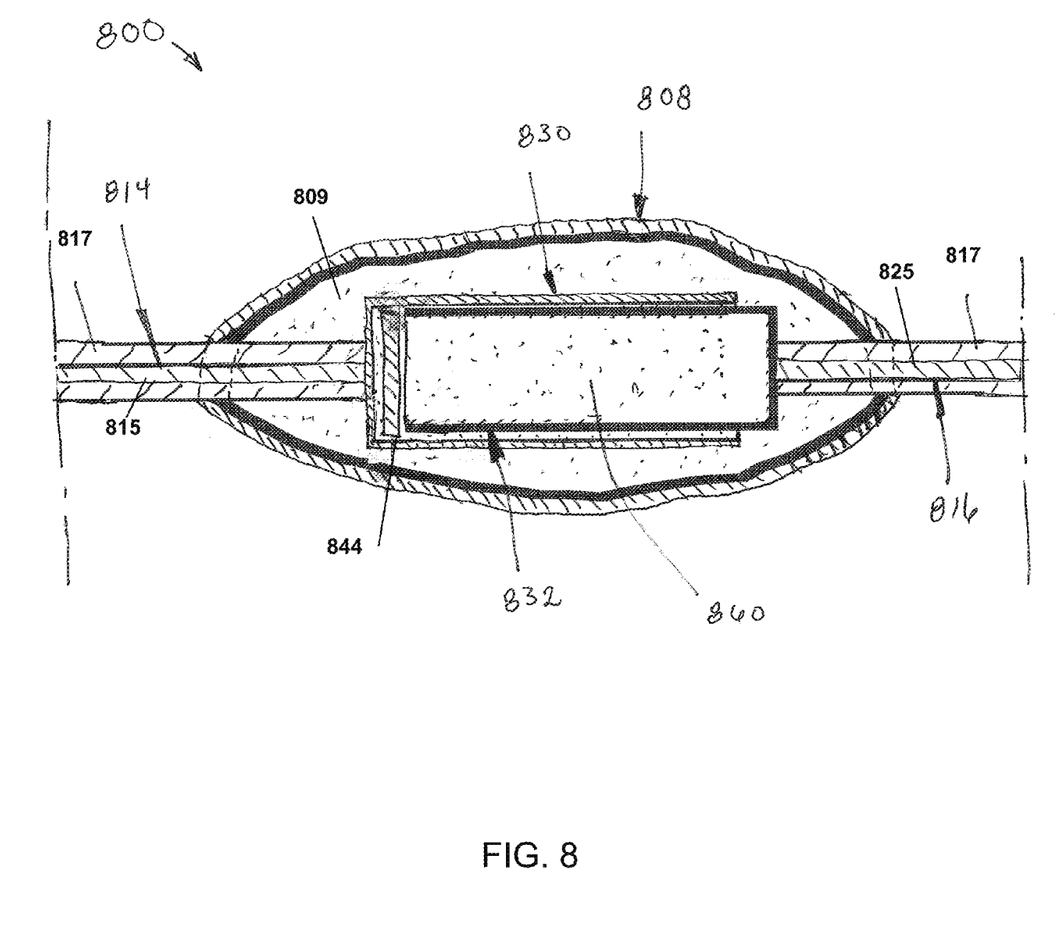
FIG. 8 shows a cutaway side view of a portion of an FSC in accordance with embodiments of the present system.

FIG. 8 shows a cutaway side view of a portion of an FSC 800 in accordance with embodiments of the present system. The FSC 800 may be similar to the FSC 100 and may include an outer cover 808 which may define at least part of a cavity 809 in which a a conductive material (e.g., an ionic fluid solution such as electrolyte saline or other suitable ionic solution or fluid) 860 may be located. First and second SLWs 814, 816, respectively, may be coupled to adjacent portions of first and second cylinders 830, 832 such as to respective end walls of the first and second cylinders 830, 832 via respective conductive layers 815, 825. The first and second SLWs 814, 816, respectively, may include a suitable insulator such as insulation 817 which may electrically insulate a corresponding one of respective conductive layers 815, 825 of the first and second SLWs 814, 816, respectively.

The outer cover 808 may be formed from any suitable material such as a polymer, silicon, silicon composite (e.g., Silastic™) which may form a seal around the cavity 809 to contain the conductive material. However, other materials for the outer cover 808 such as ceramic, etc., are also envisioned. In accordance with embodiments of the present system, the outer cover 808 may be formed by one or more layers of material, such as two or more layers of material (e.g., illustratively shown as two layers of material) one or more of which (e.g., an inner layer) may seal the cavity 809. While the outer cover 808 is illustratively shown as being ovoid-shaped, other shapes may also be suitably employed in accordance with embodiments of the present system.

In accordance with embodiments of the present system, the fluid 860 may situated about the contacts of the first and second cylinders 830, 832 including within one or more cavities thereof. In this way, transmission of electrical impulses between the first cylinder 830 and the second cylinder 832 may occur via the fluid 860 as further described herein. A disc 844 may act as a bumper to physically and/or electrically separate the first and second cylinders 830, 832, respectively, from each other.

Figure 9:
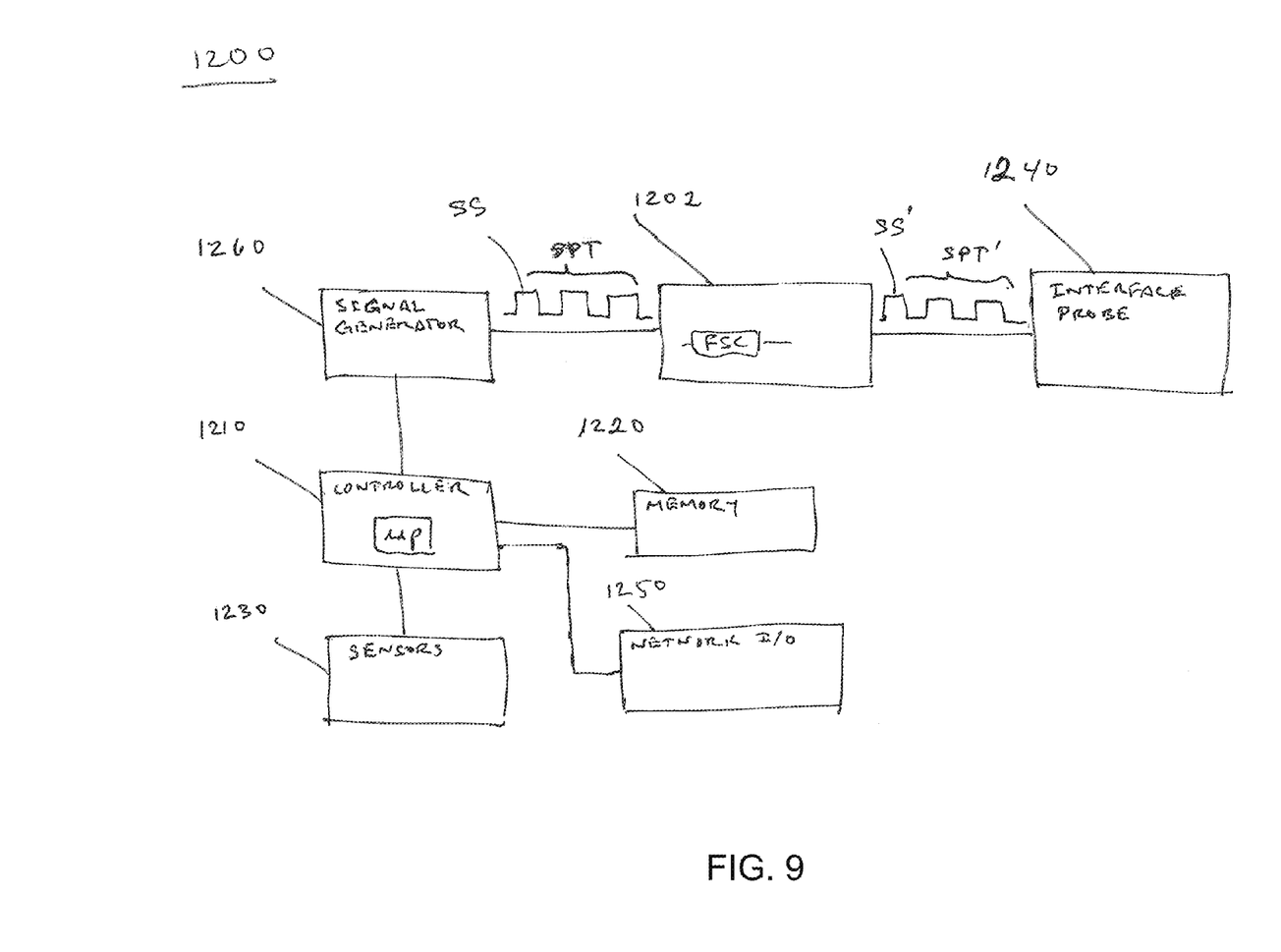
FIG. 9 shows a portion of a system in accordance with embodiments of the present system.

FIG. 9 shows a portion of a system 1200 in accordance with embodiments of the present system. For example, a portion of the present system 1200 may include one or more of an FSC 1202, an interface probe 1240, a processor 1210 (e.g., a controller), a memory 1220, sensors 1230, a signal generator 1260, and a network interface 1250. The probe 1240 (such as an implanted interface probe or the like) may be coupled to desired tissue such as cardiac tissue, nerves tissue, etc.). The processor 1210 may be operationally coupled to one or more of the memory 1220, the sensors 1230, the signal generator 1260, and the network interface 1250. One or more of the elements shown in FIG. 9 may be implanted into a patient or more be external to the patient. Though the signal generator 1260 is illustratively shown as separate from the processor 1210, it is readily appreciated that the signal generator 1260 may be provided as a portion of the processor 1210.

The memory 1220 may be any type of device for storing application data as well as other data related to the described operation. The application data and other data are received by the processor 1210 for configuring (e.g., programming) the processor 1210 to perform operation acts in accordance with the present system. The processor 1210 so configured becomes a special purpose machine particularly suited for performing in accordance with embodiments of the present system. The processor 1210 may communicate with a user and/or an external device such as an external telemetry device, so as to receive information from the user and/or external device via a network 1250. The network 1250 may include any suitable network such as a proprietary network, an input/output (I/O) port, a telephony network, a wide-area network (WAN), a local-area network (LAN), the Internet, an intranet, or (wireless personal-area networks (WPANs), a wireless network such as Bluetooth, Zigbee, WiFi, etc.

The FSC 1202 may include one or more suitable FSCs operative in accordance with embodiments of the present system and which may be coupled to each other in a serial and/or in a parallel arrangement. In embodiments wherein more than one FSC is coupled together, consideration of coupled lead lengths is provided to avoid a coupled length that is receptive to an induced standing wave from RF emissions of an MR system as described herein.

The operation acts may include configuring the system 1200 by, for example, configuring the processor 1210 to obtain information from any suitable source such as from the sensors 1230, the interface 1240, and/or the memory 1220 and processing this information in accordance with embodiments of the present system to obtain information desired by the system such as feedback information. For example, the sensors 1230 may include sensors which may detect vitals of a patient in which the system 1200 and/or portions thereof may be implanted. The processor 1210 may then use this feedback information in accordance with one or more desired algorithms to determine a desired stimulus signal (SS) and control the signal generator 1260 to generate the desired SS which may be included within a stimulus pulse train (SPT). The signal generator 1260 may then provide the SPT to the FSC 1202 which may remove any undesirable RF components which may be induced when subject to signals from external systems such as an external MRI system which may generate RF signals. These RF signals may induce an undesired RF component within the SPT. The FSC 1202 may include one or more FSCs in accordance with embodiments of the present system and may receive the input SPT and may condition the SPT to output a corresponding SPT (SPT') which may be provided to the interface probe 1240. The interface probe 1240 may then output the SPT'. For example, the interface probe 1240 may output the conditioned SPT' to a desired object such as to tissue of a patient in which the system 1200 or portions thereof may be implanted.

Figure 10:
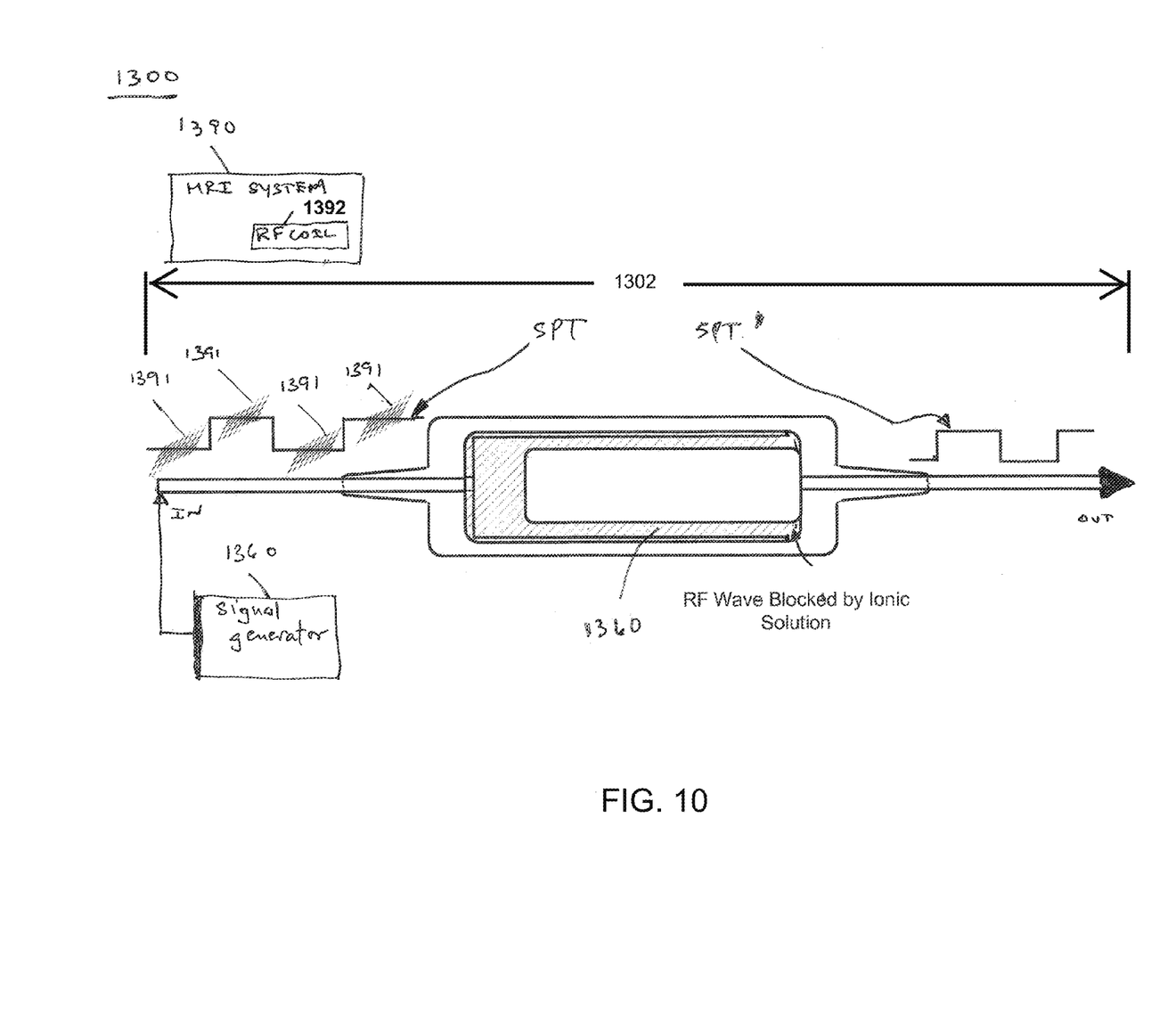
FIG. 10 which shows a block diagram illustrating an FSC operating in accordance with embodiments of the present system within an MRI system having an RF coil which may transmit RF signals.

This process is illustrated with reference to FIG. 10 which shows a block diagram illustrating a system 1300 operating in accordance with embodiments of the present system including an MRI system 1390 having an RF coil 1392 which may transmit RF signals. An SPT (e.g., as an input SPT signal (SPT)) may be generated by a signal generator 1360 and may be provided as an input to an FSC 1302. However, due to various circumstances, such as an external MRI system 1390, etc., the input SPT signal SPT may include an undesirable RF component 1391 (e.g., generated due to induced currents within the MRI system such as due to RF signals from the RF coil 1392, etc.). The FSC 1302 operating in accordance with embodiments of the present system may block this RF signal at fluid (e.g., ionic solution, ionic fluid, etc.) 1360 which may act as an attenuating fluid. For example, the fluid 1360 within the FSC 1302 may block RF waves within the input SPT signal (SPT) and output a corresponding SPT signal (SPT') as an output signal. Thus, the RF signals may be fully or substantially inhibited or attenuated in the output SPT signal (SPT'). In accordance with embodiments of the present system, the FSC 1302 may have a total lead wire length (lead length ((LEAD)) for example as indicated by a length between the arrows in the figure) greater than one-half of the MRI system's RF signal.

Referring back to FIG. 9, the system 1200 may further provide a user interface (UI) portion (UIP) which may include any suitable user interface (UI) such as a keyboard, a mouse, a trackball and/or other device, including touch-sensitive displays, which may be stand alone or be a part of a system, such as part of a personal computer, a notebook computer, a netbook, a tablet, a smart phone, a personal digital assistant (PDA), a mobile phone, and/or other device for communicating with the processor 1210 via any operable link. The UIP may be operable for interacting with the processor 1210 including enabling interaction within a UI as described herein. Clearly the processor 1210, the memory 1220, the sensors 1230, the interface probe 1240, the FSC 1202, the signal generator 1260, and/or the UIP may all or partly be a portion of a computer system or other device such as a client and/or server, an implanted medical device, and/or the like.

The methods of the present system are particularly suited to be carried out by processor programmed by a computer software program, such program containing modules corresponding to one or more of the individual steps or acts described and/or envisioned by the present system. The processor 1210 may be operable for providing control signals and/or performing operations in response to input signals from the UIP, the sensors 1230, as well as in response to other devices of a network and executing instructions stored in the memory 1220. For example, the processor 1210 may obtain feedback information from the sensors 1230 and may process this information to determine how to drive the signal generator 1260 to emit a desired SPT. The sensors 1230 may include the interface probe 1240 so as to provide a feedback signal to the controller 1210 such as the coupling FSC 1202 or may utilize a different coupling similar to the FSC 1202 in a case wherein the sensors are implanted. In this way, induced RF signals may be blocked by the FSC 1202. In accordance with embodiments of the present system, the FSC 1202 may be bidirectional thereby transmitting signals to and receiving signals from the interface probe 1240.

The processor 1210 may include one or more of a microprocessor, an application-specific or general-use integrated circuit(s), a logic device, etc. Further, the processor 1210 may be a dedicated processor for performing in accordance with the present system or may be a general-purpose processor wherein only one of many functions operates for performing in accordance with the present system. The processor 1210 may operate utilizing a program portion, multiple program segments, or may be a hardware device utilizing a dedicated or multi-purpose integrated circuit. Further variations of the present system would readily occur to a person of ordinary skill in the art and are encompassed by the following claims.

Figure 11A:
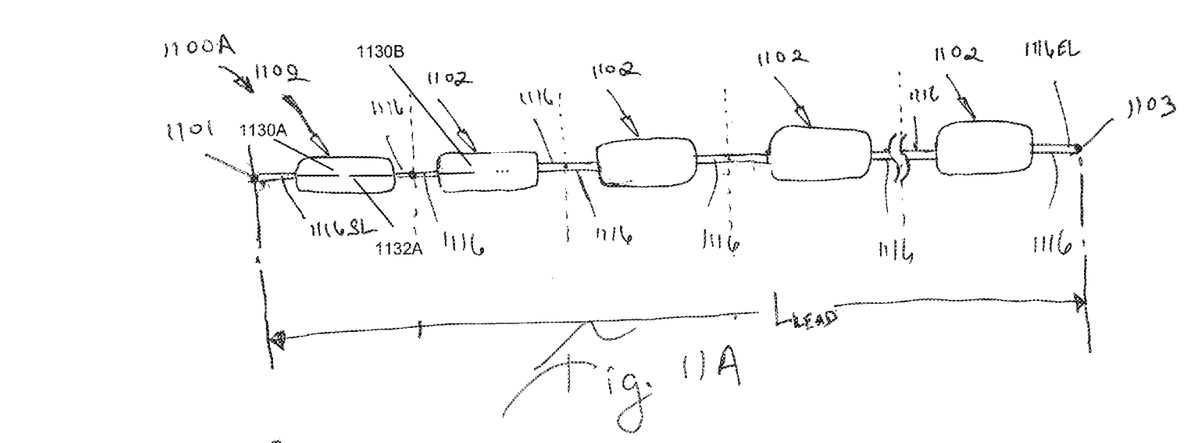
FIG. 11A shows a block diagram of a portion of a lead having a plurality of FSCs coupled together in series in accordance with embodiments of the present system.
Figure 11B:
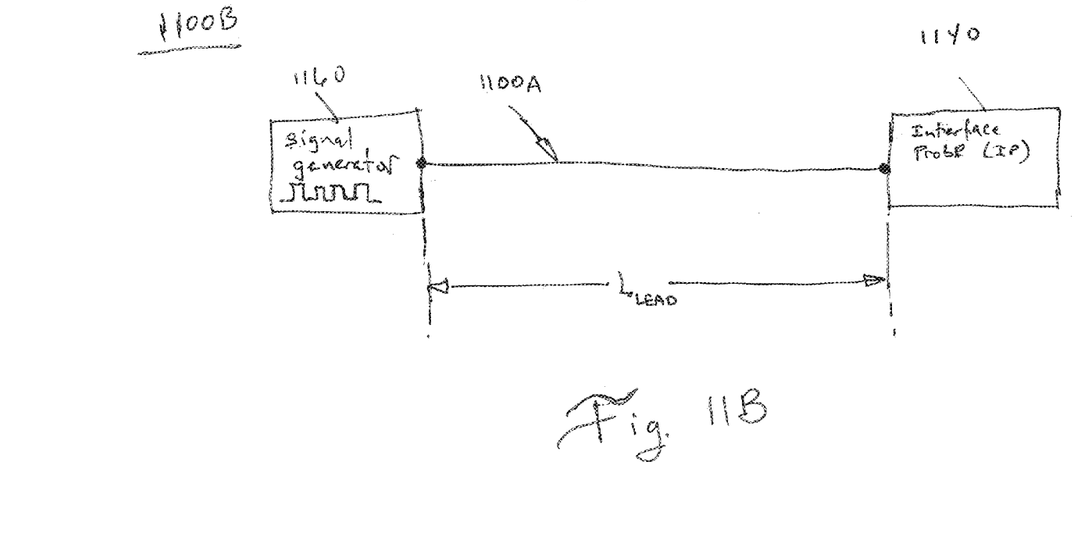
FIG. 11B shows a block diagram of a portion of an implantable medical device including the lead situated between and coupling a signal generator and an interface probe (IP) such as an implantable cardiac probe in accordance with embodiments of the present system.

FIG. 11A shows a block diagram of a portion of a lead 1100A having a plurality of FSCs 1102 (e.g., nodes) coupled together in series in accordance with embodiments of the present system. FIG. 11B shows a block diagram of a portion of an IMD 1100B including the lead 1100A situated between and coupling a signal generator 1160 and an interface probe (IP) 1140 such as an implantable cardiac probe in accordance with embodiments of the present system. Referring to FIG. 11A, SLWs 1116 may be coupled to corresponding FSCs 1102. The lead 1100A may include first and second ends 1101 and 1103, respectively, defining a length ($L_{LEAD}$) along which at least one FSC 1102 may be located. The length ($L_{LEAD}$) is shown as a straight (or substantially straight) line for the sake of clarity. However, without limitation it should be understood that this length may include other shapes such a curved line, etc. For example, it is envisioned that the lead 1100A may include a loop, a curve, a fold, etc. located along a length thereof. The IMD may be any suitable IMD such as a cardiac pacemaker, a defibrillator, or other neurostimulation devices (e.g., a phrenic nerve stimulators, deep brain stimulators, cochlear implants or vagal nerve stimulators). The IMD may be implanted within a biological object such as patient, an animal, etc.

As illustratively shown, one or more FSCs 1102 may each be coupled together in series and/or in parallel as may be desired. At least one of the lead segments 1116 (such as a start lead segment 1116SL) may receive a signal from a signal generator and this signal (e.g., a drive signal) may be coupled to another of the lead segments 1116 (such as to an end lead segment 1116EL) via a fluid coupling of each FSC 1102 so as to attenuate signals induced by radiofrequency (RF) signals of an MR system (e.g., an MR imaging (MRI) or MR spectrography (MRS) systems) and pass the drive signal. Accordingly, during operation, the drive signal may be free of interference caused by, for example, MR signals such as MR induced signals and/or RF interference generated by an MR system such as may be encountered during an MRI scan. In accordance with embodiments of the present system, the lead 1100A may have a total lead wire length (e.g., from the start lead segment 1116SL to the end lead segment 1116EL) greater than one-half wavelength length of the MRI system's RF signal and may be composed of segments having segment lengths less than one-half of a wavelength length. For example, a distance from the first end 1101 to a distal end 1130A of a contact may be composed of a segment length less than one-half of a wavelength length. Similarly, a distance from a distal end 1132A of a contact to a distal end 1130b of a next contact may be composed of a segment length less than one-half of a wavelength length. In this way a desired lead length (LEAD) may be formed while still providing any given segment length being less than one-half of a wavelength length.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. A lead wire assembly apparatus for an implantable medical device (IMD), the apparatus comprising:
    a lead having first and second ends and a plurality of separate conductive segments serially located therebetween;
    a cover defining at least one cavity situated about ends of adjacent conductive segments; and
    a fluid located in the at least one cavity, with the fluid configured to couple a signal from a first one of the adjacent conductive segments to a second one of the adjacent conductive segments.

2. The apparatus of claim 1, wherein the fluid electrically couples adjacent conductive segments to pass driving signals of the implantable medical device.

3. The apparatus of claim 2, wherein the fluid further attenuates induced signals generated by radiofrequency (RF) signals of a magnetic resonance (MR) system.

4. The apparatus of claim 1, wherein the first and second ends of the lead wire define a length of the lead (LEAD) which is greater than one-half wavelength length of radiofrequency (RF) signals generated by an MRI system.

5. The apparatus of claim 4, wherein a length of at least one of the plurality of conductive segments is less than one-half wavelength length of the radiofrequency (RF) signals generated by the MR system.

6. The apparatus of claim 1, wherein the fluid comprises a buffer.

7. The apparatus of claim 1, wherein the fluid comprises a conductive fluid.

8. A lead wire assembly apparatus for an implantable medical device (IMD), the apparatus comprising:
    a lead having first and second ends and a plurality of separate conductive segments serially located therebetween;
    a cover defining at least one cavity situated about ends of adjacent conductive segments; and
    a fluid located in the at least one cavity and coupling the adjacent conductive segments to each other, wherein the fluid comprises an ionic solution.

9. A lead wire assembly apparatus for an implantable medical device (IMD), the apparatus comprising:
    a lead having first and second ends and a plurality of separate conductive segments serially located therebetween;
    a cover defining at least one cavity situated about ends of adjacent conductive segments; and
    a fluid located in the at least one cavity and coupling the adjacent conductive segments to each other, wherein the cavity is a first cavity and ends of adjacent conductive segments are located within the first cavity coupled to corresponding conductive cylinders with a first conductive cylinder of the corresponding conductive cylinders sized to fit within a second cavity formed by a second conductive cylinder of the corresponding conductive cylinders.

10. A lead wire assembly apparatus for an implantable medical device (IMD), the apparatus comprising:
   a lead having first and second ends and a plurality of separate conductive segments serially located therebetween;
   a cover defining at least one cavity situated about ends of adjacent conductive segments; and
   a fluid located in the at least one cavity and coupling the adjacent conductive segments to each other, wherein the lead is situated between and coupled to a signal generator and an interface probe.

11. An implantable medical device, the device comprising:
   a signal generator configured to generate a driving signal;
   at least one controller configured to control the signal generator to generate the driving signal;
   a lead including first and second ends and a plurality of separate conductive segments serially located therebetween with the first end coupled to the signal generator, a cover defining at least one cavity, and a fluid located in the at least one cavity with the fluid configured to couple the driving signal between adjacent conductive segments; and
   an interface probe coupled to the second end of the lead.

12. The device of claim 11, wherein the fluid electrically couples adjacent conductive segments to pass the driving signal to the interface probe.

13. The device of claim 12, wherein the fluid further attenuates induced signals generated by radiofrequency (RF) signals of a magnetic resonance (MR) system.

14. The device of claim 11, wherein the first and second ends of the lead define a length ($L_{LEAD}$) of the lead which is greater than one-half wavelength length of radiofrequency (RF) signals generated by an MR system.

15. The device of claim 14, wherein a length of at least one of the plurality of conductive wire segments is less than one-half wavelength length of the radiofrequency (RF) signals generated by the MR system.

16. An implantable medical device, the device comprising:
   a signal generator configured to generate a driving signal;
   at least one controller configured to control the signal generator to generate the driving signal;
   a lead including first and second ends and a plurality of separate conductive segments serially located therebetween with the first end coupled to the signal generator, a cover defining at least one cavity, and a fluid located in the at least one cavity with the fluid electrically coupling adjacent conductive segments to each other; and
   an interface probe coupled to the second end of the lead, wherein the fluid comprises a buffer.

17. An implantable medical device, the device comprising:
   a signal generator configured to generate a driving signal;
   at least one controller configured to control the signal generator to generate the driving signal;
   a lead including first and second ends and a plurality of separate conductive segments serially located therebetween with the first end coupled to the signal generator, a cover defining at least one cavity, and a fluid located in the at least one cavity with the fluid electrically coupling adjacent conductive segments to each other; and
   an interface probe coupled to the second end of the lead, wherein the fluid comprises a conductive fluid.

18. The device of claim 11, wherein the fluid comprises an ionic solution.

19. The device of claim 11, wherein the cavity is a first cavity and ends of adjacent conductive segments are located within the first cavity coupled to corresponding conductive cylinders with a first conductive cylinder of the corresponding conductive cylinders sized to fit within a second cavity formed by a second conductive cylinder of the corresponding conductive cylinders.

20. A method of forming a lead for attenuating signals induced by radiofrequency (RF) signals of a magnetic resonance (MR) system, the method comprising acts of:
   forming a lead having first and second ends and a plurality of separate conductive segments serially located therebetween;
   forming a cover defining at least one cavity in which adjacent ends of conductive segments are located; and
   coupling a signal from a first one of adjacent conductive segments to a second one of the adjacent conductive segments within the at least one cavity using a fluid to perform the coupling.

* * * * *